(12) United States Patent
Banju et al.

(10) Patent No.: US 12,036,495 B2
(45) Date of Patent: *Jul. 16, 2024

(54) PLANAR FILTERING DEVICE WITH DIFFERENTLY SIZED THROUGH HOLES

(71) Applicant: Murata Manufacturing Co., Ltd., Nagaokakyo (JP)

(72) Inventors: Masaru Banju, Nagaokakyo (JP); Junko Watanabe, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 430 days.

This patent is subject to a terminal disclaimer.

(21) Appl. No.: 17/159,469

(22) Filed: Jan. 27, 2021

(65) Prior Publication Data

US 2021/0146286 A1  May 20, 2021

Related U.S. Application Data

(63) Continuation of application No. 15/964,613, filed on Apr. 27, 2018, now Pat. No. 10,940,413, which is a (Continued)

(30) Foreign Application Priority Data

Aug. 30, 2016 (JP) .................................. 2016-167715

(51) Int. Cl.
*B01D 39/10* (2006.01)
*B01D 29/11* (2006.01)
(Continued)

(52) U.S. Cl.
CPC ............ *B01D 39/10* (2013.01); *B01D 29/112* (2013.01); *B01D 39/16* (2013.01); *B01D 39/20* (2013.01);
(Continued)

(58) Field of Classification Search
USPC ....................................................... 210/650
See application file for complete search history.

(56) References Cited

U.S. PATENT DOCUMENTS

2003/0044572 A1    3/2003   Beall et al.
2008/0248182 A1   10/2008   Jongsma et al.
(Continued)

FOREIGN PATENT DOCUMENTS

CN    103285640 A    9/2013
JP    2006102720 A   4/2006
(Continued)

OTHER PUBLICATIONS

International Search Report issued for PCT/JP2017/026689 date of mailing Oct. 10, 2017.
(Continued)

*Primary Examiner* — Hayden Brewster
(74) *Attorney, Agent, or Firm* — ArentFox Schiff LLP

(57) ABSTRACT

A filter includes a plurality of first through holes which are periodically formed. At least one of the plurality of first through holes is divided by a plurality of second through holes that are smaller than the first through holes. With such a configuration, the cell aggregate having the desired size can be easily sampled.

23 Claims, 5 Drawing Sheets

Related U.S. Application Data continuation of application No. PCT/JP2017/026689, filed on Jul. 24, 2017.

(51) Int. Cl.
    *B01D 39/16*     (2006.01)
    *B01D 39/20*     (2006.01)
    *C12M 1/00*     (2006.01)
    *C12M 3/06*     (2006.01)

(52) U.S. Cl.
    CPC ......... *B01D 39/2068* (2013.01); *C12M 47/02* (2013.01); *C12M 3/06* (2013.01)

(56) References Cited

U.S. PATENT DOCUMENTS

| | | | |
|---|---|---|---|
| 2010/0255250 A1* | 10/2010 | Komori | B01D 46/247 428/116 |
| 2013/0288360 A1 | 10/2013 | Jeon et al. | |
| 2016/0252436 A1 | 9/2016 | Jeon et al. | |

FOREIGN PATENT DOCUMENTS

| | | |
|---|---|---|
| JP | 2007536071 A | 12/2007 |
| JP | 2009180594 A | 8/2009 |
| JP | 2014501499 A | 1/2014 |

OTHER PUBLICATIONS

Written Opinion of the International Searching Authority issued for PCT/JP2017/026689 date of mailing Oct. 10, 2017.

\* cited by examiner

PLANAR FILTERING DEVICE WITH DIFFERENTLY SIZED THROUGH HOLES

CROSS REFERENCE TO RELATED APPLICATIONS

The present application is a continuation of U.S. application Ser. No. 15/964,613, filed Apr. 27, 2018, which is a continuation of International application No. PCT/JP2017/026689, filed Jul. 24, 2017, which claims priority to Japanese Patent Application No. 2016-167715, filed Aug. 30, 2016, the entire contents of each of which are incorporated herein by reference.

BACKGROUND OF THE INVENTION

The present invention relates to a filter, a filtering device, and a method of filtering using the filter.

For culturing of cells, sampling devices have been developed so as to sample cells contained in culture solutions for checking culture states of the cells dipped in the culture solutions. See, for example, Japanese Unexamined Patent Application Publication No. 2009-180594.

There is a problem with the foregoing sampling device in that cell aggregates having a desired size cannot be easily sampled.

When culturing cell aggregates or the like used to, for example, investigate medicinal effects, it is required that the cell aggregates having a desired size be cultured to reduce variation of medicinal data. Accordingly, in order to check a culture state of the cell aggregates having the desired size, it is required to sample the cell aggregates having the desired size. However, cell aggregates sampled with the device described in Japanese Unexamined Patent Application Publication No. 2009-180594, in which the cell aggregates are sampled by introducing a culture solution from a culture bath to the outside through culture solution discharge piping, include cell aggregates having different sizes. In order to sample cell aggregates having a desired size from a culture solution, it is required that filtering be performed at least twice. Specifically, the filtering includes (i) filtering for removing from the culture solution cell aggregates having larger sizes than the desired size, and (ii) filtering for removing cell aggregates having smaller sizes than the desired size. Thus, in order to sample cell aggregates having a desired size from a culture solution, it is required to perform a plurality of steps. This takes a significant effort.

In order to easily sample cell aggregates having a desired size from a culture solution, the inventors studied extraction of some of the cell aggregates having the desired size during filtering for removing from the culture solution cell aggregates having larger sizes than the desired size. As a result, the inventors found a filter in which at least one of a plurality of first through holes is divided so as to form a plurality of second through holes smaller than the first through holes. The present invention was conceived on the basis of this finding.

BRIEF SUMMARY OF THE INVENTION

In accordance with one aspect of the invention, a filter comprises:
a base member having a plurality of first through holes, each first though hole having a first cross-sectional area; and
the base member also having at least one through hole cluster comprising a plurality of second through holes, each through hole of the through hole cluster having a second cross-sectional area which is smaller than the cross-sectional area of each of the first through holes.

In a preferred aspect of the invention, a ratio of an area occupied by the second through holes to a surface area of a first main surface of the base member is smaller than a ratio of an area occupied by the first through holes to the surface area of the first main surface of the base member.

In accordance with a preferred embodiment of the invention a principal component of the filter is at least one of metal and a metal oxide.

In another preferred aspect of the invention, the cross-sectional area of each of the first through holes is within 10% of a design cross-sectional area and at least one of the through hole clusters has an outer dimension with a cross sectional area which is within 10% of the design cross-sectional area of the first through holes.

In other aspects of the invention, the at least one through hole cluster comprises a plurality of through hole clusters. In some embodiments, each of the through hole clusters is divided into the same number of second through holes. In other embodiments, at least two of the through hole clusters is divided into a different number of second through holes.

The present invention is also directed towards a filtering device, comprising the above described filter supported by a container unit having an inlet through which a cell-aggregate-containing liquid can be introduced and passed through the filter and an outlet through which the cell-aggregate-containing liquid and having been passed through the filter can be discharged.

The invention is further directed towards a method of filtering, comprising passing a cell-aggregate-containing liquid through at least one filter having the structure of the filter described above.

In one aspect of the invention, a ratio of an area occupied by the second through holes to a surface area of a first main surface of the base member is smaller than a ratio of an area occupied by the first through holes to the surface area of the first main surface of the base member.

In a preferred embodiment, when the cell-aggregate-containing liquid is passed through one of the filters, a first cell aggregate is captured at the first through holes of the one of the filters, and a second cell aggregate that is smaller than the first cell aggregate is captured at the second through holes of the one of the filters.

In another embodiment of the invention, the at least one filter comprises first and second filters, the first filter having at least one through hole cluster divided into second through holes which are smaller than the first through holes of the first filter, the second filter having second through holes which are smaller than the second through holes of the first filter. In this embodiment, the cell-aggregate-containing liquid is first passed through the first filter and is then passed through the second filter whereby first and second cell aggregates are captured by the first and second through holes of the first filter and third cell aggregates, which are smaller than the first and second cell aggregates, are captured by the second thorough holes of the second filter.

With the present invention, cell aggregates having a desired size can be easily sampled.

DESCRIPTION OF THE PREFERRED EMBODIMENTS

First Embodiment

[Filter]

Figure 1:
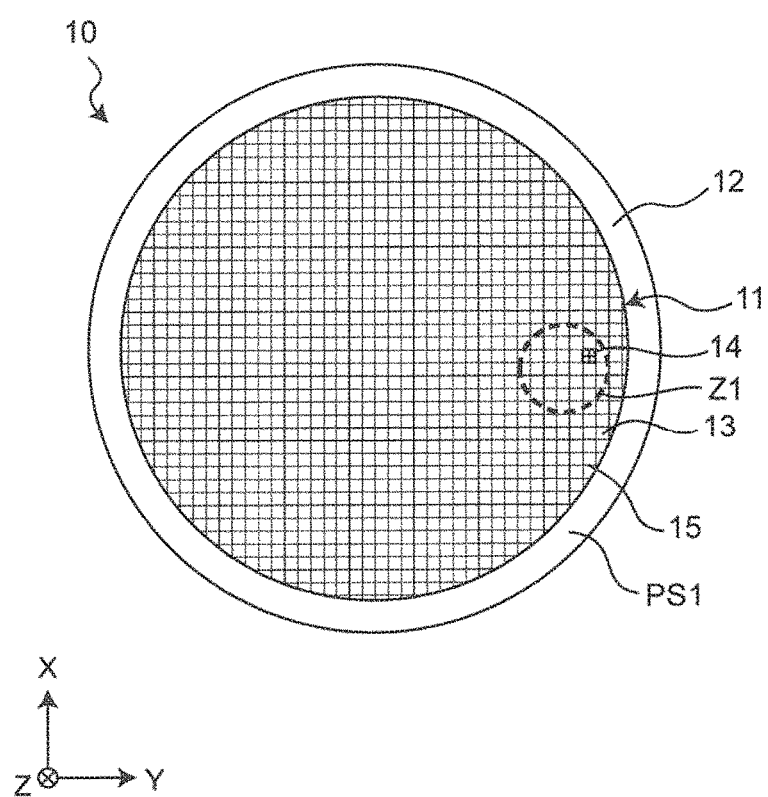
FIG. 1 is a schematic view of a filter according to a first embodiment of the present invention.
Figure 2:
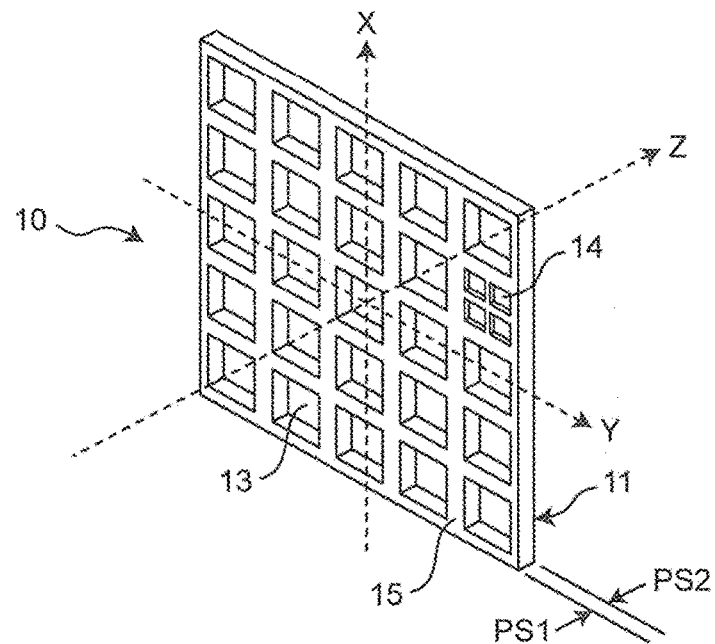
FIG. 2 is an enlarged perspective view of a Z1 portion of the filter illustrated in FIG. 1.

FIG. 1 is a schematic view of a filter 10 according to a first embodiment of the present invention. FIG. 2 is an enlarged perspective view of a square subsection of the filter 10 taken from the area Z1 in FIG. 1. The X, Y, and Z directions in FIGS. 1 and 2 respectively indicate longitudinal, transverse, and thickness directions of the filter 10.

As illustrated in FIG. 1, the filter 10 includes a base member 11 having a plurality of through holes formed therein and a frame portion 12 provided at an outer circumference of the base member 11. As illustrated in FIG. 2, the base member 11 has first and second opposed main surfaces PS1 and PS2. A plurality of first through holes 13 are periodically formed in the base member 11. Each of the first through holes has the same outer dimension (in the disclosed embodiment a square having four sides of length d). At least one through hole cluster 14 is formed in the base member 11. The through hole cluster 14 has the same overall dimensions as the first through holes 13 but is divided into a plurality of smaller through holes (in this embodiment, four smaller through holes).

The filter 10 filters cell aggregates having larger sizes than a desired size when a culture solution (liquid) containing cell aggregates having different sizes passes through the base member 11. In so doing, cell aggregates having the desired size are sampled with the filter 10.

The term "cell aggregates" herein mean aggregates of cells each formed of a plurality of cells adhering to one another. Examples of cells included in the cell aggregate include, for example, cancerous cells, stem cells, induced pluripotent stem cells (iPS cells), ES cells, mesenchymal stem cells, and regenerative medicine cells. Herein, examples of the liquid include, for example, culture solutions containing an amino acid, protein, serum, or the like, phosphate buffer physiological saline, and water. In addition to the cell aggregates and the liquid, the cell-aggregate-containing liquid may also contain a non-biologically originated substance such as a resin particle, part of a tissue such as a bone fragment or a flesh fragment, and a dead cell.

According to the first embodiment, the base member 11 is, for example, a circular metal mesh. The dimensions of the base member 11, for example, 8 mm in diameter and 15 μm in thickness. Furthermore, the principal component of the base member 11 is at least one of metal and a metal oxide. The material of the base member 11 may be, for example, gold, silver, copper, platinum, nickel, or palladium, or an alloy or an oxide of any of these. The shape of the base member 11 is not limited to a circular shape. For example, the shape of the base member 11 may be a polygon shape such as a rectangle or a square or another shape such as an ellipse.

<Base Member>

As illustrated in FIGS. 1 and 2, the base member 11 is a plate-shaped structure in which the plurality of first through holes 13 and the one or more through hole clusters 14 are formed. According to the first embodiment, the filter 10, and with it the base member 11, has a circular shape. However, the shape of the filter 10 is not limited to a circular shape. For example, the shape of the filter 10, and with it (or independently of it) the base member 11 may be any other desired shape, for example a parallelepiped shape such as a rectangle or a square or another shape such as an ellipse.

Figure 3:
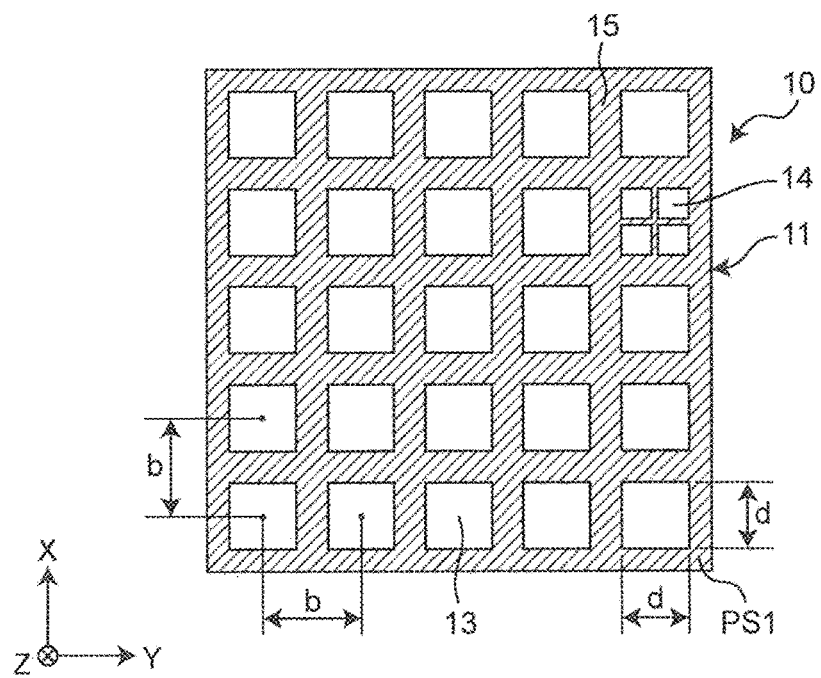
FIG. 3 is a schematic view of part of a filter portion illustrated in FIG. 2 when seen in the thickness direction.

FIG. 3 is a schematic view of a square sub-portion of the base member 11 when viewed in the thickness direction (Z direction). As illustrated in FIG. 3, the plurality of first through holes 13 extend from a first main surface PS1 of the base member 11 to the second main surface PS2 of the base member 11. The through holes 13 are periodically disposed throughout square sub portion shown (and preferably throughout the base member 11). Specifically, in the first embodiment, the plurality of first through holes 13 are equally spaced and arranged in a matrix shape in the base member 11. In other word, the plurality of first through holes 13 are arrayed in a lattice.

According to the first embodiment, the first through holes 13 each have a square shape when seen from the first main surface PS1 side of the base member 11, that is, seen in the Z direction. The shape of the first through hole 13 seen in the Z direction is not limited to a square and may be, for example, a circle, an ellipse, or a polygon such as a rectangle.

According to the first embodiment, the shape of the first through hole 13 projected onto a plane lying perpendicular to the first main surface PS1 of the base member 11 (sectional shape) is a rectangle. Specifically, the sectional shape of the first through hole 13 is a rectangle in which the length of a side in a radial direction of the filter 10 is longer than the length of a side in the thickness direction of the filter 10. The sectional shape of the first through hole 13 is not limited to a rectangle and may be, for example, a parallelogram or a tapered shape such as a trapezoid. The sectional shape of the first through hole 13 may be symmetric or asymmetric.

According to the first embodiment, the plurality of first through holes 13 are equally spaced apart from one another in two array directions parallel to the corresponding sides of the squares when seen from the first main surface PS1 side (seen in the Z direction) of the base member 11, that is, in the X direction and the Y direction in FIG. 3. When the plurality of first through holes 13 are arranged in the square lattice array as described above, the opening ratio can be increased, and accordingly, passage resistance of the culture solution containing the cell aggregates against the filter 10 can be reduced. With such a configuration, processing time can be reduced with the result that stress applied to the cell aggregates can be reduced. Furthermore, the symmetry of the array of the plurality of first through holes 13 is improved, and accordingly, observation of the filter is facilitated.

The array of the plurality of first through holes 13 is not limited to the square lattice array and may be, for example, a quasi-periodic array or a periodic array. The periodic array may be, for example, a rectangular array in which distances in the two array directions are not equal as long as it is a quadrate array. Also, the periodic array may be a triangular lattice array or a regular triangle lattice array. It is sufficient that the base member 11 have the plurality of first through holes 13. How the plurality of first through holes 13 are arrayed is not limited.

The distance between the first through holes 13 is appropriately designed in accordance with the types (size, form, property, and resilience) or the amount of the cell aggregates to be isolated from the culture solution. The distance between the first through holes 13 means, as illustrated in FIG. 3, a distance b between the centroid (e.g., center) of any of the first through holes 13 and the centroid of the different adjacent first through hole 13 when seen from the first main surface PS1 side of the base member 11. According to the first embodiment, the centroid of the first through hole 13 is a point where the two diagonal lines of the square-shaped first through hole 13 intersect each other. In the case of a periodically arrayed structure, the distance b between the first through holes 13 is, for example, larger than the length of a side d of the first through holes 13 and equal to or smaller than ten times the length of the side d of the first through holes 13, and preferably, equal to or smaller than three times the length of the side d of the through holes 13. Alternatively stated, for example, the opening ratio of the first through holes 13 in the base member 11 is 10% or larger, and preferably, 25% or larger. With such a configuration, resistance of the culture solution containing the cell aggregates against the base member 11 can be reduced. Accordingly, processing time can be reduced, thereby the stress applied to the cell aggregates can be reduced. The opening ratio of the first through holes 13 is calculated as follows: (the area occupied by the first through holes 13)/(the projection area of the first main surface PS1 when it is assumed that no first through hole 13 or through hole cluster 14 is formed therein).

The dimensions of the first through holes 13 are designed so that cell aggregates having larger sizes than a desired size (first cell aggregates) can be captured. That is, the first through holes 13 are designed so that cell aggregates having sizes equal to or smaller than the desired size can pass through the first through holes 13 and cell aggregates having larger sizes than the desired size are captured (e.g., accumulated) at the first main surface at locations corresponding to the first through holes 13. Furthermore, the plurality of first through holes 13 are preferably designed so that the dimensions of the plurality of first through holes 13 are substantially the same. The phrase "designed so that the dimensions of the plurality of first through holes 13 are substantially the same" means that the dimensional deviation of the first through holes 13 is within 10% of a nominal design dimension.

The openings of each of the first through holes 13 on the first main surface PS1 side and the second main surface PS2 side preferably communicate with each other through continuous wall surfaces. Specifically, the opening of the first through hole 13 on the first main surface PS1 side can be projected onto the opening of the first through hole 13 on the second main surface PS2 side. That is, when the base member 11 is seen from the first main surface PS1 side, the opening of the first through hole 13 on the first main surface PS1 side is superposed on the opening of the first through hole 13 on the second main surface PS2 side. According to the first embodiment, inner walls of the first through hole 13 are perpendicular to the first main surface PS1 and the second main surface PS2.

The through hole cluster 14 is formed by effectively subdividing one of the plurality of first through holes 13 into smaller second through holes 15. [As discussed below, more than one through hole cluster can be formed in the base member 11.] According to the first embodiment, four second through holes 15 are formed by dividing the through hole cluster 14 into four subparts. Furthermore, in this embodiment the through hole cluster 14 is preferably formed at a position near the frame portion 12.

The dimensions of the second through holes 15 are designed so that cell aggregates having the desired size (second cell aggregates) can be captured (e.g., accumulated). That is, the second through holes 15 are designed so that the second cell aggregates that are smaller than the first cell aggregates are captured on the first main surface PS1 at the locations of the second through holes 15. With such a configuration, some of the cell aggregates having the desired size can be captured at the second through holes 15.

According to the first embodiment, the configuration of the second through holes 15 is similar to that of the first through holes 13 except that they are smaller in cross-sectional area than the first through holes. That is, when seen from the first main surface PS1 side of the base member 11, that is, seen in the Z direction, the plurality of second through holes 15 are arrayed in a lattice and each have a square shape. However, the configuration of the plurality of second through holes 15 may be different from the configuration of the first through holes 13. The array of the plurality of second through holes 15 is not limited to the square lattice array and may be, for example, a quasi-periodic array or a periodic array. The shape of the second through holes 15 seen in the Z direction is not limited to a square and may be, for example, a circle, an ellipse, or a polygon such as a rectangle.

The ratio of the area occupied by the second through holes 15 to the surface area of the first main surface PS1 of the filter 10 is preferably smaller than that of the first through holes 13. In other words, the design opening ratio of the second through holes 15 is smaller than the opening ratio of the first through holes 13. The opening ratio of the second through holes 15 is calculated as follows: (the area occupied by the second through holes 15)/(the projection area of the first main surface PS1 when it is assumed that no first through holes 13 or second through holes 15 are formed therein). For example, the opening ratio of the second through holes 15 is smaller than 10%, and preferably, from 1 to 5%.

The thickness of the base member 11 is preferably from more than 0.01 to ten times the size (side d) of the sides of the first through holes 13. More preferably, the thickness of the base member 11 is from more than 0.02 to five times the size (side d) of the first through holes 13. With such a configuration, while the mechanical strength of the filter 10 is ensured, passage resistance of the culture solution containing the cell aggregates can be reduced, and accordingly, the processing time can be reduced. As a result, the stress applied to the cell aggregates can be reduced.

In the base member 11, the first main surface PS1 to be brought into contact with the culture solution containing the cell aggregates may be smooth. Specifically, the first main surface PS1 of the base member 11 may be a flat surface that is even and without irregularities. In other words, the openings of the plurality of first through holes 13 and the openings of the plurality of second through holes 15 on the first main surface PS1 of the base member 11 are preferably formed on a single plane. Furthermore, a portion of the base member 11 where neither the first through holes 13 nor the second through holes 15 are formed is continuous and integrally formed. With such a configuration, the first cell aggregates captured at the first through holes 13 and the second cell aggregates captured at the second through holes 15 can be easily collected. Furthermore, since the first main surface PS1 of the base member 11 is smooth, observation with a microscope can be easily performed. For example, the cell aggregates captured on the first main surface PS1 can be observed by directly carrying the filter 10 in which the cell aggregates are captured to a microscope. At this time, since the first main surface PS1 is even and flat without irregularities, operations such as focusing can be easily performed even under a high magnification.

<Frame Portion>

The frame portion 12 is provided along an outer circumference of the base member 11. The number of the first through holes 13 per unit area is preferably smaller in the frame portion 12 than the rest of the base member 11. The number of the first through holes 13 in the frame portion 12 is preferably 1% or less of the number of the first through holes 13 in the base member 11. The thickness of the frame portion 12 may be larger than the thickness of the base member 11. With such a configuration, the mechanical strength of the filter 10 can be improved.

In the case where the filter 10 is connected to a device in use, the frame portion 12 also functions as a connecting portion (reference sign 19 in FIG. 4 to be described later) that connects the filter 10 to the device. Furthermore, information relating to the filter 10 (such as the dimensions of the first through holes 13 and the second through holes 14) may be marked in the frame portion 12.

As illustrated in FIG. 1, the frame portion 12 has a ring shape when seen from the first main surface PS1 side of the base member 11. When the filter 10 is seen from the first main surface PS1 side, the center of the frame portion 12 is aligned with the center of the base member 11. That is, the frame portion 12 is formed on a concentric circle of the base member 11.

[A Filtering Device]

Figure 4:
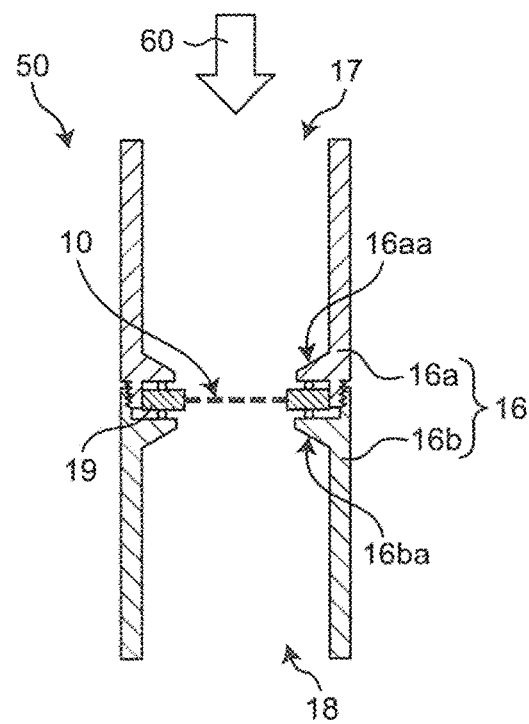
FIG. 4 is a schematic view of a filtering device according to the first embodiment of the present invention.

A filtering device 50 is described with reference to FIG. 4 which is a schematic view of the filtering device 50 according to the first embodiment of the present invention. As illustrated in FIG. 4, the filtering device 50 includes a container unit 16 and the filter 10 disposed in the container unit 16. According to the first embodiment, the filter 10 is connected to the container unit 16 through the connecting portion 19 of the filter 10.

<Container Unit>

The container unit 16 is a cylindrical body that has an inlet 17 through which a cell-aggregate-containing liquid is introduced and an outlet 18 through which the liquid is discharged. In this embodiment, the container unit 16 has a cylinder-shape. However, it is sufficient that the container unit 16 have a flow passage therein through which a liquid flows, and the shape of the container unit 16 is not limited to a cylindrical shape. The container unit 16 may have, for example, an elliptical shape, a square shape, or a rectangular shape when seen from the inlet 17 side.

The container unit 16 may be formed of, for example, a material that can be gamma sterilized. The container unit 16 may be formed of a material that contains, for example, polyethylene, polyethylene terephthalate, polyurethane, polystyrene, silicon rubber, ABS resin, polyamide, polyamideimide, polysulfone, natural rubber, latex, urethane rubber, silicon rubber, ethylene vinylacetate, polyesters, epoxies, phenols, silica, alumina, gold, platinum, nickel, stainless steel, titanium, or the like. With the container unit 16 formed of such a material, the stress applied to the cell aggregates can be reduced.

According to the first embodiment, the container unit 16 includes two members: a first member 16a and a second member 16b. The first member 16a and the second member 16b are connected to each other, for example, by screwing at threaded portions formed at respective end portions. A first projection 16aa and a second projection 16ba are respectively formed on inner walls of the first member 16a and the second member 16b so as to hold the frame portion 12 of the filter 10. When the first member 16a and the second member 16b are connected to each other, the frame portion 12 of the filter 10 is held between the first projection 16aa and the second projection 16ba with the connecting portion 19 interposed therebetween. With such a configuration, the filter 10 is disposed between the inlet 17 and the outlet 18 of the container unit 16. Thus, when the cell-aggregate-containing liquid is introduced through the inlet 17 of the container unit 16, the liquid passes through the filter 10 disposed in the container unit 16 and then discharged through the outlet 18.

According to the first embodiment, the filtering device 50 allows the cell-aggregate-containing liquid to pass through the filter 10, for example, due to gravity applied downward in the vertical direction to the first main surface PS1 of the filter 10, that is, the self weight of the liquid. In order to cause the cell-aggregate-containing liquid to pass through the filter 10, the filtering device 50 may include a pressure unit that applies pressure to the liquid in a direction 60 from the inlet 17 toward the outlet 18 of the container unit 16 while the liquid is in contact with the first main surface PS1 of the filter 10. Alternatively, the filtering device 50 may include a suction unit that sucks the liquid in the direction 60 from the second main surface PS2 side while the liquid is in contact with the first main surface PS1 of the filter 10. With the pressure unit and/or the suction unit, the filtering device 50 can reduce filtering time. In the case of applying the pressure or suction, the force is preferably set to such a degree that the cell aggregates are not deformed.

In the filtering device 50, the first member 16a can be separated from the second member 16b after the cell-aggregate-containing liquid has been filtered with the filter 10. Then, the filter 10 in which the cell aggregates have been captured can be set in a microscope while the filter 10 remains attached to the second member 16b. Thus, the cell aggregates captured by the filter 10 can be easily observed. As a result, with the filtering device 50, a culture state of the cell aggregates having the desired size having been captured at the second through holes 14 can be easily checked.

[A Method of Filtering]

A method of filtering with the filter 10 is described.

First, the filter 10 is prepared. For example, the filter 10 is attached to the container unit 16. Specifically, the connecting portion 19 is attached to the frame portion 12 of the filter 10, and after that, the filter 10 is disposed on the second projection 16ba of the second member 16b. Next, the first member 16a is connected to the second member 16b so that the first projection 16aa of the first member 16a is in contact with the connecting portion 19. The first member 16a and the second member 16b are connected to each other by screwing the first member 16a into the second member 16b at the threaded portions. Thus, the connecting portion 19 attached to the frame portion 12 of the filter 10 is held by the first projection 16aa and the second projection 16ba.

Next, the cell-aggregate-containing liquid is caused to pass through the filter 10. Specifically, the liquid is caused to flow inside the container unit 16 from the inlet 17 toward the outlet 18 of the container unit 16, thereby the liquid passes through the base member 11. Thus, the filter 10 captures the cell aggregates.

Examples of a method of causing the cell-aggregate-containing liquid to pass through the filter 10 include, for example, a method with which the liquid is caused to pass through from above under the influence of gravity in the vertical direction with respect to the first main surface PS1 of the base member 11. Other than the above-described method, the examples of the method of causing the cell-aggregate-containing liquid to pass through the filter 10 also include, for example, the following methods: a method with which a pressure is applied to the liquid in the direction 60 from the inlet 17 toward the outlet 18 of the container unit 16 while the liquid is in contact with the first main surface PS1 of the filter 10; and a method with which the liquid is sucked in the direction 60 from the second main surface PS2 while the liquid is in contact with the first main surface PS1 of the base member 11. When causing the cell-aggregate-containing liquid to pass through the base member 11, it is preferable that the stress applied to the cell aggregates be reduced as much as possible. For example, in the case of applying the pressure, the pressure is preferably set to such a degree that the cell aggregates are not deformed. It is more preferable that the liquid be caused to pass through the base member 11 due to the self weight of the liquid without application of the pressure. Also, it is preferable that the opening ratio of the base member 11 be increased so as to reduce the processing time, thereby reducing the time period during which the stress is applied to the cell aggregates.

According to the first embodiment, the dimensions of the first through holes 13 of the base member 11 are designed so that the first cell aggregates having larger sizes than the desired size can be captured. Furthermore, the plurality of second through holes 15 are designed so that the second through holes 15 are formed by effectively dividing a through hold cluster 14 into four second smaller second through holes 15. Specifically, the outer dimensions of the through hole cluster is preferably within 10% of the outer dimensions of the design value of the first through holes 14 and the dimensions of the second through holes 14 are designed so that the second cell aggregates having a smaller size than the sizes of the first cell aggregates, that is, the cell aggregates having the desired size, can be captured at the second through holes 15.

Accordingly, the first cell aggregates having larger sizes than the desired size can be captured at the first through holes 13 by causing the cell-aggregate-containing liquid to pass through the base member 11, and some of the second cell aggregates having the desired size can be extracted at the second through holes 15. That is, with the method of filtering, the first cell aggregates can be removed and the second cell aggregates having the desired size can be sampled by performing filtering once.

[Advantages]

The filter 10 according to the first embodiment can provide the following advantages.

The filter 10 has the plurality of first through holes 13 periodically formed therein, and at least one of through hole cluster 14 containing one or more through holes 15 which are smaller in cross-sectional dimension than the first thorough holes 13, such that during filtering of the first cell aggregates having larger sizes are captured at the first through holes 13 and at least some second cell aggregates having sizes are captured at the second through holes 15.

Thus, with the filter 10, the cell aggregates having at least two desired sizes can be easily sampled without performing filtering a plurality of times.

In the design, the ratio of the area occupied by the second through holes 15 to the surface area of the first main surface PS1 of the filter 10 is smaller than that of the first through holes 13. With such a configuration, the cell aggregates having larger sizes than the desired size can be efficiently filtered at the first through holes 13, and the cell aggregates having the desired size can be easily sampled at the second through holes 15. Furthermore, the cell aggregates having sizes equal to or smaller than the desired size can pass through the first through holes 13. This can suppress clogging and reduce the pressure applied to the base member 11 during filtering.

The principal component of base member 11 is preferably at least one of metal and a metal oxide. With such a configuration, the mechanical strength of the filter 10 can be improved compared to that of a resin filter such as a membrane. With the filter 10, for example, the cell aggregates captured at the first and second through holes 13 and 15 are unlikely to be deformed while the cell-aggregate-containing liquid is passing through the base member 11. This can suppress passage of cell aggregates having the desired size through the base member 11.

The filtering device 50 and the method of filtering also provide similar advantages to the above-described advantages of the filter 10. In particular, with the filtering device 50, handleability of the filter 10 can be improved. For example, the cell aggregates captured on the first main surface PS1 of the base member 11 can be easily observed by a microscope while the filter 10 remains attached to the second member 16b of the container unit 16.

Although the example in which the principal component of the filter 10 is at least one of metal and a metal oxide is described for the first embodiment, this is not required. It is sufficient that the filter 10 is a porous film. For example, the filter 10 may be formed of nylon, polypropylene, polyethylene, polyester, polyetherether ketone, polyethylene terephthalate, polyvinylidene chloride, or the like.

Although the example in which the first cell aggregates are captured at the first through holes 13 and the second cell aggregates are captured at the second through holes 15 is described for the first embodiment, this is not limiting. Matter other than the cell aggregates may be captured at the first and second through holes 13 and 15. For example, isolated cells may be captured at the first through holes 13. Furthermore, the second through holes 15 may be used to identify the matter other than the cell aggregates having passed through the first through holes 13. That is, the second through holes 15 may be used to obtain presence information of substances contained in the liquid by capturing them at the second through holes 15 the substances present in the liquid having passed through the first through holes 13. The second through holes 15 may be used to obtain presence information of, for example, isolated cells, dead cells, resin beads, and so forth.

Although the example in which the second through holes 15 are formed on the frame portion 12 side of the base member 11 (see FIG. 1) is described for the first embodiment, the invention is not so limited. The second through holes 15 may be formed at any position of the base member 11 where the cell-aggregate-containing liquid passes through. For example, the second through holes 15 may be formed at the center or the peripheral end of the base member 11.

IN the first embodiment the through hole cluster 14 is formed of four second through holes 15. However, the invention is not so limited. It is sufficient that the through hole cluster 14 have one or more through holes that are smaller than the first through holes 13 (e.g., within 10% smaller than the design dimensions of the first through holes 13). Furthermore, while a single through hole cluster 14 is shown in the foregoing embodiment, a plurality of such clusters can be provided.

Figure 5:
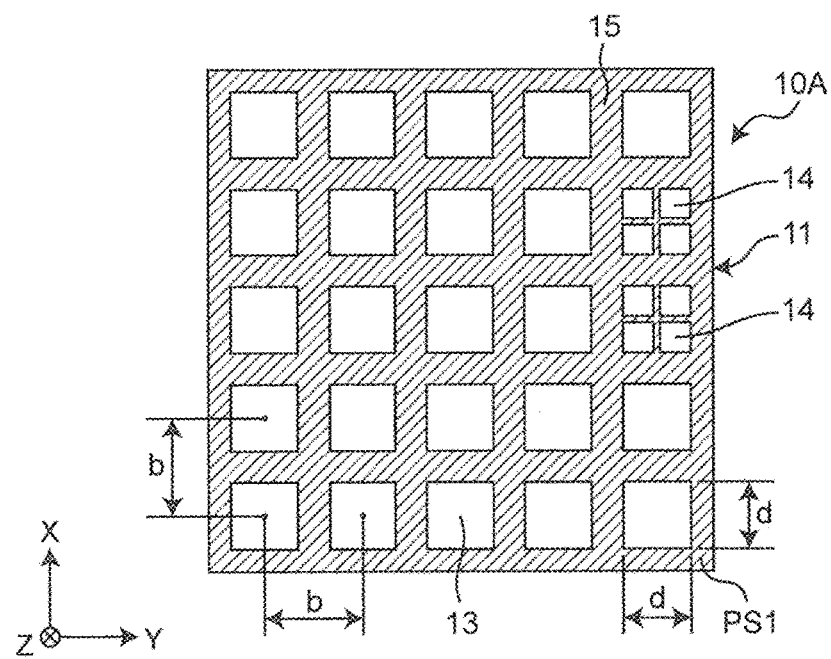
FIG. 5 illustrates a filter according to a variant of the first embodiment of the present invention.

For example, FIG. 5 illustrates a filter 10A according to a variant of the first embodiment of the present invention. As illustrated in FIG. 5, in the filter 10A, a plurality of through hole clusters 14, each containing four second through holes 15, are provided. The number of samples of the cell aggregates having the desired size can be increased by increasing the ratio of the area occupied by the second through holes 15 to the surface area of the first main surface PS1 of the filter 10A as described above. Although the through hole clusters 14 are shown as being adjacent to one another in FIG. 5, they may be formed in other areas of the base member 11 (and need not be adjacent).

Figure 6:
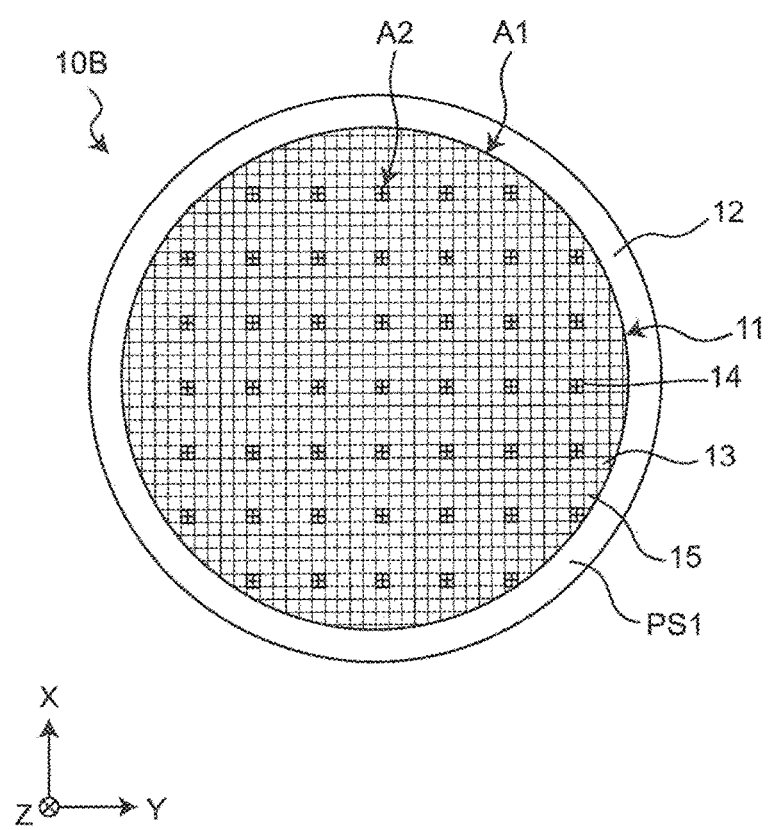
FIG. 6 illustrates a filter according to another variant of the first embodiment of the present invention.

FIG. 6 illustrates a filter 10B according to another variant of the first embodiment of the present invention. As illustrated in FIG. 6, regions A2, where the through hole clusters 14 are formed, are distributed over a region A1 where the first through holes 13 are formed. The region A1 where the first through holes 13 are formed is a region where the base member 11 can be seen from the first main surface PS1 side of the base member 11. The regions A2 where the through hole clusters 14 are formed is a region where the through hole clusters 14 are formed in the base member 11 when the filter 10B is seen from the first main surface PS1 side.

As illustrated in FIG. 6, a plurality of regions A2 where the through hole clusters 14 are formed are spaced from one another by a specified distance in the region A1 where the first through holes 13 are formed. With such a configuration, the cell aggregates having the desired size can be more easily sampled. Furthermore, the cell aggregates having the desired size can be sampled from the cell-aggregate-containing liquid (or gas) passing through any regions of the base member 11 of the filter 10B. Although the configuration is described in which the plurality of regions A2 where the through hole clusters 14 are formed are spaced from one another by a specified distance in the region A1 where the first through holes 13 are formed in the filter 10B illustrated in FIG. 6, the invention is not so limited. It is sufficient that the regions A2 where the through hole clusters 14 are formed be distributed over the region A1 where the first through holes 13 are formed. For example, the regions A2 where the through hole clusters 14 are formed may be randomly provided in the region A1 where the first through holes 13 are formed. Furthermore, the regions A2 where the through hole clusters 14 are formed may be distributed over only part of the region A1 where the first through holes 13 are formed. As described above, the number and/or positions of the regions A2 where the through hole clusters 14 are formed may be appropriately changed.

Figure 7:
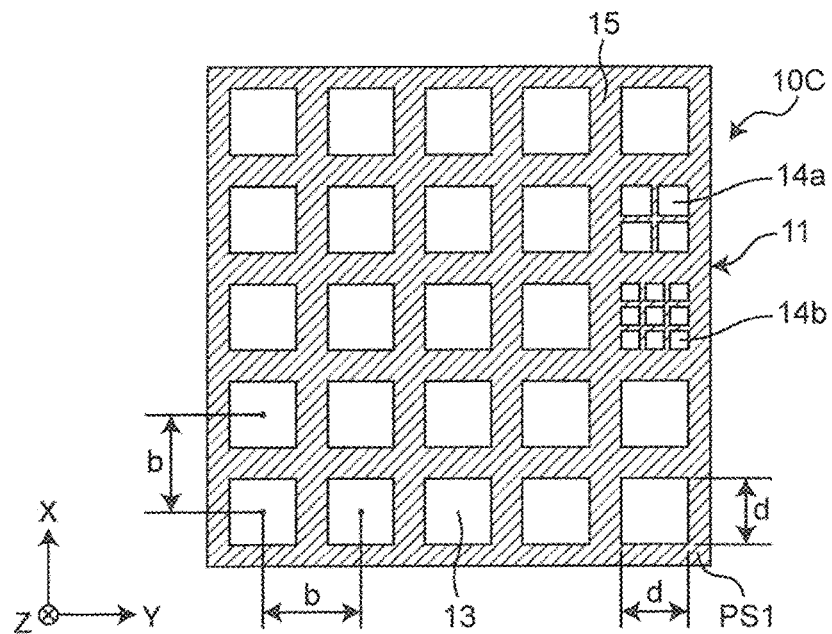
FIG. 7 illustrates a filter according to another variant of the first embodiment of the present invention.

FIG. 7 illustrates a filter 10C according to another variant of the first embodiment of the present invention. As illustrated in FIG. 7, through hole clusters may have different numbers (and sized) of second through holes. In this embodiment, a first through hole cluster 14-1 is formed of four second through holes 15a and a second through hole cluster 14-2 is formed of nine, smaller, second through holes 15b. As a result, cell aggregates of a second size can be captured by the larger second through holes 15a and smaller third aggregates can be captured by the smaller second through holes 15b. Thus, during filtering of the first cell aggregates having larger sizes than the desired size, cell aggregates of two different desired sizes can be easily sampled. In other words, the cell aggregates having different sizes can be easily sampled by performing filtering once.

Although the example in which the through holes 15a and 15b of two sizes that are smaller than the first through holes 13 are described with reference to FIG. 7, the filter 10C is not limited to this. The number of through holes having different sizes may be determined in accordance with the number of sizes of the cell aggregates a user wishes to sample.

In the foregoing embodiment, the through hole cluster 14-1 is divided into four through holes 15a, each of which is of the same size. Similarly, the through hole cluster 14-2 is divided into nine smaller through holes 15b, each of which has the same size. However, the invention is not so limited. Either or both of the through hole clusters can be divided into a plurality of through holes of different sizes, some larger than the others.

Although the example in which the container unit 16 of the filtering device 50 includes two members, that is, the first member 16a and the second member 16b is described for the first embodiment, the invention is not so limited. Furthermore, although the example in which the first member 16a and the second member 16b are connected to each other by screwing at the screw portions is described for the first embodiment, the invention is not so limited. For example, the first member 16a and the second member 16b of the container unit 16 may be integrally formed.

Although the example in which the filter 10 is disposed between the inlet 17 and the outlet 18 of the container unit 16 in the filtering device 50 is described for the first embodiment, the invention is not so limited. It is sufficient that the filter 10 be disposed at a position where the cell-aggregate-containing liquid can pass. For example, the filter 10 may be disposed at the inlet 17 or the outlet 18 of the container unit 16.

Figure 8:
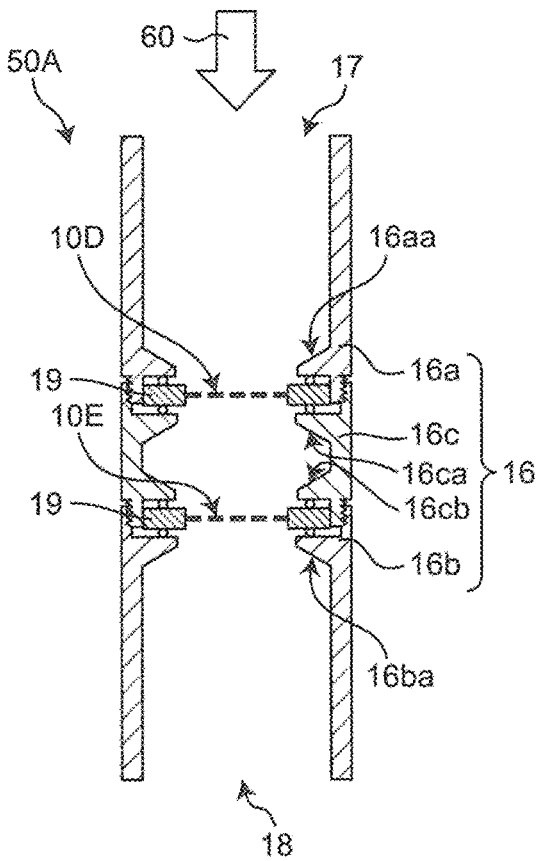
FIG. 8 illustrates a filtering device according to a variant of the first embodiment of the present invention.

Although the example in which the filtering device 50 includes a single filter 10 is described for the first embodiment, the invention is not so limited. The filtering device 50 may include a plurality of filters 10. For example, FIG. 8 illustrates a filtering device 50A according to a variant of the first embodiment of the present invention. As illustrated in FIG. 8, in the filtering device 50A, a first filter 10D may be disposed between the inlet 17 and the outlet 18 of the container unit 16 and a second filter 10E may be disposed closer to the outlet 18 side of the container unit 16 than the first filter 10D. The first filter 10D and the second filter 10E may be the same or different from each other.

When the first filter 10D and the second filter 10E are the same, the number of samples of the cell aggregates having the desired size can be increased.

When the first filter 10D and the second filter 10E are different from each other, the cell aggregates having different sizes can be sampled at the respective filters. For example, thorough hole clusters 14 having relatively large second through holes 15 may be provided in the first filter 10D and through hole clusters having relatively small second through holes 15 may be provided in the second filter 10E. With such a configuration, it is possible, for example, to extract first cell aggregates having large sizes at the first through holes 13 of the first filter 10D, extract some of the second cell aggregates having a smaller size at the second through holes 15 of the first filter 10D and extract yet smaller third cell aggregates at the second through holes 15 of the second filter 10E.

The container unit 16 of the filtering device 50A includes three members, that is, a first member 16*a*, a second member 16*b*, and a third member 16*c*. Specifically, as illustrated in FIG. 8, the third member 16*c* is provided between the first member 16*a* and the second member 16*b*. A third projection 16*ca* and a fourth projection 16*cb* are formed in the third member 16*c* so as to hold the filter 10D and the filter 10E. Thus, a frame portion 12 of the first filter 10D is held by a first projection 16*aa* of the first member 16*a* and the third projection 16*ca* of the third member 16*c*. Also, a frame portion 12 of the second filter 10E is held by a second projection 12*ba* of the second member 16*b* and the fourth projection 16*cb* of the third member 16*c*.

Also in the method of filtering, the number of samples may be increased and the cell aggregates having different sizes may be sampled by causing the cell-aggregate-containing liquid to pass through the plurality of filters 10 as described above.

Although the present invention is sufficiently described in relation to the preferred embodiment with reference to the accompanying drawings, a variety of variants and modifications are obvious to those skilled in the art. It should be understood that such variants and modifications are included within the scope of the present invention as far as those variants and modifications do not depart from the scope of present invention defined by the attached claims.

With the filter according to the present invention, cell aggregates having a desired size can be easily sampled. Accordingly, this filter is useful for sampling cell aggregates having a desired size from a culture solution.

REFERENCE SIGNS LIST

10, 10A, 10B, 10C, 10D, 10E filter
11 base member
12 frame portion
13 first through hole
14, 14-1, 14-2 though hole cluster
15, 15*a*, 15*b* second through hole
16 container unit
16*a* first member
16*aa* first projection
16*b* second member
16*ba* second projection
16*c* third member
16*ca* third projection
16*cb* fourth projection
17 inlet
18 outlet
19 connecting portion
50, 50A filtering device
60 direction
PS1 first main surface
PS2 second main surface

The invention claimed is:

1. A filter comprising:
 (a) a planar base member having opposed first and second surfaces;
 (b) a plurality of first through holes extending from the first surface to the second surface, each of the first through holes having:
  (i) first and second open ends located at the first and second surfaces, respectively, whereby fluid to be filtered can enter the first through hole at the first open end and exit the first through hole at the second open end; and
  (ii) the same shape and substantially the same cross-sectional area as the other first through holes; and
 (c) a first through hole cluster comprising a plurality of adjacent second through holes, each of the second through holes extending from the first surface to the second surface and having:
  (i) third and fourth open ends located at the first and second surfaces, respectively, whereby fluid to be filtered can enter the second through hole at the third open end and exit the second through hole at the fourth open end; and
  (ii) the same shape and substantially the same cross-sectional area as the other second through holes, the cross-sectional area of the second through holes being smaller than the cross-sectional area of the first through holes.

2. The filter of claim 1, wherein the first through hole cluster has a shape and outer periphery that is the same as the shape and outer periphery of the first through holes.

3. The filter of claim 1, wherein a principal component of the base member is at least one of metal and a metal oxide.

4. The filter according to claim 1, wherein the base member has a plurality of identical first through hole clusters.

5. The filter according to claim 1, wherein the first through hole cluster has four adjacent through holes.

6. The filter according to claim 1, wherein the first through hole cluster has at least four adjacent through holes.

7. The filter according to claim 1, wherein the base member is a planar unitary member.

8. The filter according to claim 1, wherein the first through holes have a square shape.

9. The filter according to claim 8, wherein the second through holes have a square shape.

10. The filter according to claim 1, wherein the second through holes have a square shape.

11. A filtering device, comprising:
 the filter of claim 1; and
 a container unit supporting the filter, the container unit having an inlet through which a cell-aggregate-containing liquid can be introduced and passed through the filter and an outlet through which the cell-aggregate-containing liquid which has passed through the filter can be discharged.

12. The filtering device according to claim 11, wherein the first through hole cluster has a shape and outer periphery that is the same as the shape and outer periphery of the first through holes.

13. The filtering device according to claim 11, wherein a principal component of the base member is at least one of metal and a metal oxide.

14. The filtering device according to claim 11, wherein the base member has a plurality of identical first through hole clusters.

15. The filtering device according to claim 11, wherein the first through hole cluster has four adjacent through holes.

16. The filtering device according to claim 11, wherein the first through hole cluster has at least four adjacent through holes.

17. The filtering device according to claim 11, wherein the first through holes have a square shape.

18. The filtering device according to claim 17, wherein the second through holes have a square shape.

19. The filtering device according to claim 11, wherein the second through holes have a square shape.

20. The filter according to claim 1, wherein the first and second surfaces are planar surfaces and each of the first through holes has a central flow axis extending perpendicular to the planar surfaces and from the first surface to the second surface.

21. The filter according to claim 1, wherein the walls of each of the through holes are impervious to the fluid being filtered.

22. The filtering device according to claim 11, wherein the first and second surfaces are planar surfaces and each of the first through holes has a central flow axis extending perpendicular to the planar surfaces and from the first surface to the second surface.

23. The filtering device according to claim 11, wherein the walls of each of the through holes are impervious to the fluid being filtered.

* * * * *